United States Patent [19]

Funaki et al.

[11] Patent Number: 4,987,247
[45] Date of Patent: Jan. 22, 1991

[54] PRODUCTION OF TETRAHYDROPHTHALIMIDE COMPOUND

[75] Inventors: Yuji Funaki, Toyonaka; Masayuki Fukushima, Minoo, both of Japan

[73] Assignee: Sumitomo Chemical Company, Limited, Osaka, Japan

[21] Appl. No.: 409,297

[22] Filed: Sep. 19, 1989

Related U.S. Application Data

[62] Division of Ser. No. 239,470, Sep. 1, 1988.

[30] Foreign Application Priority Data

Sep. 1, 1987 [JP] Japan .................. 62-218608
Apr. 27, 1988 [JP] Japan .................. 63-107008

[51] Int. Cl.$^5$ .................. C07C 205/00
[52] U.S. Cl. .................. 560/23
[58] Field of Search .................. 560/23, 45

[56] References Cited

U.S. PATENT DOCUMENTS

4,500,719  2/1985  Oba et al. .................. 548/502
4,670,046  1/1987  Nagano et al. .................. 71/96

FOREIGN PATENT DOCUMENTS

0049508  4/1982  European Pat. Off.
59-67255  4/1984  Japan .................. 560/45

OTHER PUBLICATIONS

Sumitomo Chemical, *Chemical Abstracts*, vol. 101, No. 151490q, (1984).

*Primary Examiner*—Bruce Gray
*Attorney, Agent, or Firm*—Birch, Stewart, Kolasch & Birch

[57] ABSTRACT

A process for preparing a compound of the formula:

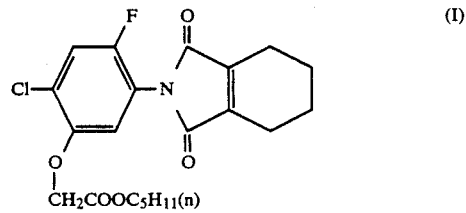

(I)

in an excellent yield with high purity, which comprises reacting a compound of the formula:

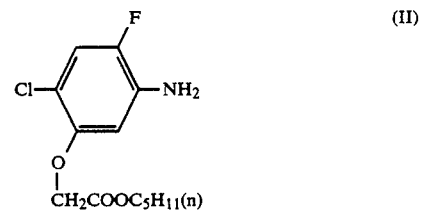

(II)

with 3,4,5,6-tetrahydrophthalic anhydride in the presence of a catalyst system consisting of a nitrogen-containing base and a lower fatty acid.

1 Claim, No Drawings

PRODUCTION OF TETRAHYDROPHTHALIMIDE COMPOUND

This application is a divisional of copending application Ser. No. 07/239,470 filed on Sept. 1, 1988.

The present invention relates to production of a tetrahydrophthalimide compound. More particularly, it relates to an improved process for preparing N-[4-chloro-2-fluoro-5-(pentyloxycarbonylmethyloxy)-phenyl]-3,4,5,6-tetrahydrophthalimide.

Said N-[4-chloro-2-fluoro-5-(pentyloxycarbonylmethyloxy)phenyl]-3,4,5,6-tetrahydrophthalimide is representable by the formula:

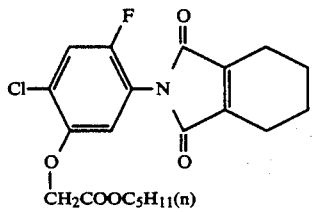

(I)

and, as described in U.S. Pat. No. 4,670,046, is per se useful as a herbicide. In said U.S. patent, the compound (I) is produced by reacting N-(4-chloro-2-fluoro-5-hydroxyphenyl)-3,4,5,6-tetrahydrophthalimide with n-pentyl haloacetate in an inert solvent. On the other hand, EP-B-0049508 discloses production of some tetrahydrophthalimide compounds by the reaction of an aniline compound with 3,4,5,6-tetrahydrophthalic anhydride in an inert solvent. However, those conventional processes can not afford the compound (I) in a satisfactorily high yield with a sufficiently high purity so that a troublesome operation such as chromatography is needed for separation or purification of the product. In addition, the use of a large amount of an organic solvent which is not easily recovered or has an unpleasant odor is required. Accordingly, said conventional processes are problematic for practical adoption, at an industrial scale.

As a result of an extensive study, it has been found that the compound (I) can be obtained in an excellent yield with a high purity by reacting an aniline compound of the formula:

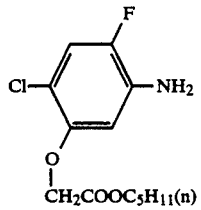

(II)

with [3,4,5,6]-tetrahydrophthalic anhydride in the presence of a catalyst system consisting of a nitrogen-containing base and a lower aliphatic acid. This invention is based on the above finding.

The reaction is carried out in an organic solvent such as hydrocarbons (e.g. toluene, xylene, benzene), halogenated hydrocarbons (e.g. 1,2-dichloroethane, chlorobenzene, chloroform, carbon tetrachloride) or ketones (e.g. methyl isobutyl ketone) at a temperature of about 50° C. to the boiling temperature of the solvent, preferably of about 80° to 120°0 C., for a period of about 1 to 10 hours.

As the nitrogen-containing base, there may be exemplified secondary amines (e.g. diethylamine, dibutylamine, diethanolamine), tertiary amines (e.g. triethylamine, tributylamine, triethanolamine, N,N-dimethylaniline, N,N-diethylaniline), nitrogen-containing heterocyclic compounds (e.g. pyridine, piperidine, imidazole, morpholine, quinoline, N,N-dimethylaminopyridine), etc. Examples of the lower aliphatic acid are acetic acid, propionic acid, butyric acid, etc.

The amount of the 3,4,5,6-tetrahydrophthalic anhydride to be used is usually from about 1.0 to 2.0 equivalents, preferably from about 1.0 to 1.3, to one equivalent of the compound (II). The amount of the nitrogen-containing base may be from about 0.01 to 0.5 equivalents, preferably from about 0.05 to 0.1 equivalents, to 1 equivalent of the compound (II), and that of the lower aliphatic acid may be from about 1.0 to 5.0 equivalents, preferably from about 1.0 to 2.0, to one equivalent of the nitrogen-containing base.

The reaction vessel may be equipped with a water separator so as to remove water by-produced in the reaction by its azeotropic distillation with the solvent, thereby resulting in acceleration of the reaction. In that case, the reaction may be effected under reduced pressure so that the boiling temperature of the solvent is lowered, and azeotropic distillation may be achieved at any desired temperature.

After completion of the reaction, the reaction mixture may be subjected to ordinary post-treatment such as addition of water, extraction with a water-immiscible solvent and concentration to recover the compound (I). Further, after removal of the solvent from the extract containing the compound (I), the crude product may be crystallized from water or its mixture with an alcohol (e.g. methanol, ethanol, isopropanol), followed by collection of the crystals.

The starting compound (II) is novel and can be produced by subjecting the corresponding nitro compound of the formula:

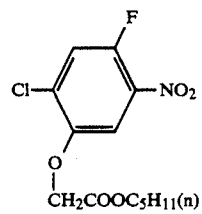

(III)

to reduction. The reduction may be accomplished by a per se conventional procedure for conversion of a nitro group into an amino group such as iron reduction or catalytic reduction.

In case of iron reduction, the compound (III) is reacted with iron powders in the presence of an acid catalyst in an inert solvent, usually at a temperature of room temperature to the boiling temperature of the solvent, preferably of about 60° to 90° C., for a period of about 0.5 to 24 hours to give the compound (II). Examples of the acid catalyst are a mineral acid (e.g. hydrochloric acid, sulfuric acid), an aliphatic acid (e.g. formic acid, acetic acid), an iron chloride (e.g. ferrous chloride, ferric chloride), etc. As the solvent, there may be used water or its mixture with an organic solvent chosen from aromatic hydrocarbons (e.g. benzene, toluene, xylene), halogenated hydrocarbons (e.g. dichloroethane, carbon tetrachloride, chlorobenzene), ketones (e.g. acetone, methyl isobutyl ketone), ethers (e.g. diethyl ether, tetrahydrofuran, dioxane), esters (e.g. ethyl acetate), aliphatic hydrocarbons (e.g. hexane, heptane), aliphatic acids (e.g. formic acid, acetic acid), etc. The amounts of iron powders may be from about 2.2 to 10 equivalents, preferably from about 3 to 5 equivalents, to one equivalent of the compound (III). The amount of the acid catalyst is usually from about 0.01 to 6.0 equivalents to one equivalent of the compound (III). When the acid catalyst is chosen from the mineral acid and the aliphatic acid, it may be used in an excessive amount so that it can play not only a role of the catalyst but also a role of the solvent.

After completion of the reaction, the reaction mixture is subjected to post-treatment by a per se conventional procedure. For instance, the reaction mixture is filtered, the filtrate is extracted with an organic solvent and the extract is concentrated. When desired, the resultant product may be purified, for instance, by distillation, recrystallization, silica gel column chromatography or the like.

In case of catalytic reduction, the compound (III) is reduced with hydrogen in the presence of a catalyst in an inert solvent under a pressure from the atmospheric pressure to 30 kg/cm$^2$. Hydrogen is used normally in an amount of 3 to 10 equivalents to one equivalent of the compound (III). The catalyst may be chosen from nickel, palladium, platinum, platinum dioxide, rhodium, etc., and its amount is normally from about 0.001 to 10% by weight, preferably from about 0.1 to 5% by weight, to the compound (III). When desired, the catalyst may used on a carrier material such as activated carbon or alumina, or in the form of a complex, for instance, with triphenylphosphine. Examples of the solvent are alcohols (e.g. methanol, ethanol, isopropanol), aromatic hydrocarbons (e.g. benzene, toluene, xylene), ketones (e.g. acetone, methyl isobutyl ketone), ethers (e.g. tetrahydrofuran, dioxane), aliphatic acids (e.g. acetic acid, propionic acid), esters (e.g. ethyl acetate), halogenated hydrocarbons (e.g. dichloroethane, chlorobenzene), water, and their mixtures. Generally, the reduction is conducted at a temperature of room temperature to the boiling point of the solvent, preferably of room temperature to 80° C., for a period of about 0.5 to 24 hours. These reaction conditions are, however, not limitative; for instance, the reaction condition may be autogenic when it is performed in an autoclave.

After completion of the reaction, the reaction mixture is, for instance, filtered to remove the catalyst, and the filtrate is concentrated to recover the compound (II). When desired, any purification procedure such as distillation, recrystallization or column chromatography may be applied to the product thus obtained.

The compound (III) is also novel and may be produced, for instance, by reacting 2-chloro-4-fluoro-5-nitrophenol with a haloacetic ester of the formula:

Y—CH$_2$COOC$_5$H$_{11}$(n)     (IV)

wherein Y is a chlorine atom or a bromine atom in the presence of a base, usually in an inert solvent at a temperature of room temperature to the boiling point of the solvent, preferably of about 50° to 90° C., for a period of about 0.5 to 24 hours. The compound (IV) and the base may be used respectively in about 1.0 to 2.0 equivalents, preferably about 1.0 to 1.3 equivalents, and in about 1.0 to 2.0 equivalents, preferably about 1.0 to 1.3 equivalents, to one equivalent of 2-chloro-4-fluoro-5-nitrophenol. Examples of the solvent are alcohols (e.g. methanol, ethanol, isopropanol), aromatic hydrocarbons (e.g. benzene, toluene, xylene), halogenated hydrocarbons (e.g. dichloroethane, carbon tetrachloride, chlorobenzene), ketones (e.g. acetone, methyl isobutyl ketone), ethers (e.g. diethyl ether, tetrahydrofuran, dioxane), nitriles (e.g. acetonitrile), aliphatic hydrocarbons (e.g. hexane, heptane), dimethylsulfoxide, dimethylformamide, water, etc. Among them, preferred are polar solvents such as nitriles and dimethylformamide, mixed solvents such as water-aromatic hydrocarbons, etc. Examples of the base are alkali metal hydroxides (e.g. sodium hydroxide, potassium hydroxide), alkali metal carbonates (e.g. sodium carbonate, potassium carbonate), alkali metal bicarbonates (e.g. sodium hydrogen carbonate), alkali metal hydrides (e.g. sodium hydride), alkali metal alkoxides (e.g. sodium methoxide), organic bases (e.g. triethylamine, pyridine, dimethylaminopyridine), etc. When desired, the reaction may be performed in the presence of a catalyst such as a metal salt (e.g. sodium bromide, potassium bromide, sodium iodide, potassium iodide) or a quarternary ammonium salt (e.g. tetrabutylammonium chloride) in an amount of about 0.001 to 0.2 equivalents to one equivalent of 2-chloro-4-fluoro-5-nitrophenol.

After completion of the reaction, the reaction mixture may be, for instance, admixed with water and extracted with an organic solvent, followed by concentration. When desired, any purification procedure such as distillation or silica gel column chromatography may be applied to give the resulting product.

Still, 2-chloro-4-fluoro-5-nitrophenol is known as disclosed in U.S. Pat. No. 4,670,046.

Practical and presently preferred embodiments of the invention are illustratively shown in the following Examples and Comparative Examples.

EXAMPLE 1

Preparation of the compound (III):

A mixture of 2-chloro-4-fluoro-5-nitrophenol (100 g), anhydrous potassium carbonate (86.6 g) and dimethylformamide (500 g) was heated at 50° C., and amyl 2-chloroacetate (90.2 g) was dropwise added thereto in 30 minutes, followed by allowing to stand at 60° C. for 4 hours. The reaction mixture was cooled to room temperature, and water (1500 g) was added thereto, followed by extraction with ethyl acetate (1500 g). The organic layer was separated, washed with water and concentrated under reduced pressure. The residue was distilled under reduced pressure to give 4-chloro-2-fluoro-5-(pentyloxycarbonylmethyloxy)nitrobenzene (Compound (III)) (129 g) as a pale yellow oil. Yield, 77%. b.p., 160°-165° C./0.7 mmHg.

NMR δ (CDCl$_3$, TMS) (ppm): 7.58 (1H, d, J=7 Hz), 7.39 (1H, d, J=10 Hz), 4.80 (2H, s), 4.22 (2H, t, J=6 Hz), 1.10–2.00 (6 H, m), 0.91 (3 H, t, J=6 Hz).

EXAMPLE 2

Preparation of the compound (II):

A mixture of iron powder (115 g), acetic acid (29 g) and water (551 g) was heated at 80° C., and a solution of the compound (III) (132 g) in acetic acid (200 g) was dropwise added thereto in 1 hour, followed by heating under reflux for 5 hours. The reaction mixture was filtered to remove insoluble materials, and the filtrate was extracted with ethyl acetate. The extract was concentrated under reduced pressure. The residue was distilled off under reduced pressure to give 4-chloro-2-fluoro-5-(pentyloxycarbonylmethyloxy)aniline (Compound (II)) (90 g). Yield, 75 b.p., 145°-149° C./0.4 mmHg. m.p., 32°-3420 C.

NMR δ(CDCl$_3$, TMS) (ppm): 7.00 (1H, d, J=10 Hz), 6.37 (1H, d, J=7 Hz), 4.60 (2H, s), 4.20 (2H, t, J=6 Hz), 3.75 (2H, brs), 1.10–1.90 (6H, m), 0.92 (3H, t, J =6 Hz).

EXAMPLE 3

Preparation of the compound (II):

Hydrogen gas (1.3 liters) was introduced into a mixture of the compound (III) (6.4 g), 5% palladium-carbon (0.32 g) and toluene (64 g) at room temperature while stirring in 1 hour. After removal of the catalyst from the reaction mixture, the solvent was removed under reduced pressure, and the residue was purified by silica gel column chromatography to give 4-chloro-2-fluoro-5-(pentyloxycarbonylmethyloxy)aniline (3.6 g). Yield, 62%.

EXAMPLE 4

Preparation of the compound (I):

A mixture of the compound (II) (12.0 g), 3,4,5,6-tetrahydrophthalic anhydride (7.56 g), piperidine (0.18 g), propionic acid (0.30 g) and toluene (24 g) was heated under reflux for 5 hours, during which water as by-produced was azeotropically removed. To the reaction mixture, toluene (24 g) and water (24 g) were added, and the organic layer was separated and concentrated under reduced pressure. To the residue, water (18 g) and methanol (33 g) were added, and the precipitated crystals were collected by filtration to give N-[4-chloro-2-fluoro-5-(pentyloxycarbonylmethyloxy)-phenyl]-3,4,5,6-tetrahydrophthalimide (Compound (I)) (16.1 g). By the use of a high speed liquid chromatography, the purity of the compound (I) as the major product and the amount of the by-produced 4-chloro-2-fluoro-5-(pentyloxycarbonylmethyloxy)acetanilide (hereinafter referred to as "N-acetyl compound") as a contaminant were determined according to the inner standard method and the area comparison method, respectively.

Yield, 92.0%.

Purity: 92.3% (N-acetyl compound content, less than 0.1%).

NMR δ (CDCl$_3$, TMS) (ppm): 7.22 (1H, d, J=10 Hz), 6.75 (1H, d, J=7 Hz), 4.6 (2H, s), 4.1 (2H, t, J=6 Hz), 2.40 (4H, m), 1.80 (4H, m), 1.10–1.80 (6H, m), 0.85 (3H, t, J=6 Hz).

IR (Nujol): 1750, 1720 (cm$^{-1}$).

m.p.: 90°–91° C.

EXAMPLE 5

Preparation of the compound (I):

A mixture of the compound (II) (12.0 g), 3,4,5,6-tetrahydrophthalic anhydride (7.56 g), triethylamine (9.42 g), acetic acid (0.75 g) and 1,2-dichloroethane (24 g) was heated under reflux for 8 hours. The reaction mixture was washed with water (24 g). The organic layer was separated and treated as in Example 4 to give the compound (I) (16.2 g).

Yield, 92.5%.

Purity: 94.7% (N-acetyl compound content, 0.1%).

EXAMPLE 6

Preparation of the compound (I):

A mixture of the compound (II) (12.0 g), 3,4,5,6-tetrahydrophthalic anhydride (7.56 g), piperidine (0.36 g), acetic acid (0.5 g) and toluene (24 g) was refluxed at 88° to 92° C. under a pressure of about 300 mmHg for 4 hours, during which water was azeotropically removed. The reaction mixture was then treated as in Example 4 to give the compound (I) (16.7 g).

Yield, 95.2%.

Purity: 97.0% (N-acetyl compound content, less than 0.1%).

COMPARATIVE EXAMPLE 1

To a solution of N-(4-chloro-2-fluoro-5-hydroxyphenyl)-3,4,5,6-tetrahydrophthalimide (3 g) in dimethylformamide (100 ml), anhydrous potassium carbonate (0.8 g) and then amyl chloroacetate (1.9 g) were added, and the resultant mixture was heated at 70° to 80° C. for 3 hours. The reaction mixture was cooled to room temperature, admixed with water and extracted with diethyl ether. The etheral layer was washed with water, dried over anhydrous magnesium sulfate and concentrated under reduced pressure. The residue was purified by silica gel column chromatography to give the compound (I) (1.8 g).

Yield, 42.0%.

Purity: 98.0%.

COMPARATIVE EXAMPLE 2

A mixture of the compound (II) (12.0 g), 3,4,5,6-tetrahydrophthalic anhydride (7.56 g) and acetic acid (50 g) was heated at 90° to 95° C. for 7 hours. The reaction mixture was cooled to room temperature, and water (75 g) was added thereto. The precipitated crystals were collected by filtration to give the compound (I) (15.7 g).

Yield, 89.3%.

Purity: 88.7% (N-acetyl compound content, 5.1%).

COMPARATIVE EXAMPLE 3

A mixture of the compound (II) (12.0 g), 3,4,5,6-tetrahydrophthalic anhydride (7.56 g) and acetic acid (50 g) was heated under reflux for 2 hours. The reaction mixture was cooled to room temperature, and water (75 g) was added thereto. The precipitated crystals were collected by filtration to give the compound (I) (15.4 g).

Yield, 88.0%.

Purity: 87.0% (N-acetyl compound content, 7.2%).

COMPARATIVE EXAMPLE 4

A mixture of the compound (II) (12.0 g), 3,4,5,6-tetrahydrophthalic anhydride (7.56 g) and toluene (50 g) was heated under reflux for 12 hours. Analysis by high speed liquid chromatography revealed the presence of 20% of the compound (II) as unreacted. The reaction mixture was concentrated under reduced pressure, and the residue was purified by silica gel column chromatography to give the compound (I) (10.9 g).

Yield, 62.0%.

Purity: 98.0%.

COMPARATIVE EXAMPLE 5

A mixture of the compound (II) (12.0 g) and 3,4,5,6-tetrahydrophthalic anhydride (7.56 g) was heated at 85° to 90° C. for 10 hours. Analysis by high speed liquid chromatography revealed the presence of 72% of the compound (I) and 9% of the compound (II) as unreacted together with many other impurities. The reaction mixture was purified by silica gel column chromatography to give the compound (I) (11.4 g).

Yield: 65.0%.
Purity: 98.2%.

COMPARATIVE EXAMPLE 6

A mixture of the compound (II) (12.0 g), 3,4,5,6-tetrahydrophthalic anhydride (7.56 g), triethylamine (0.4 g) and toluene (50 g) was heated under reflux for 10 hours. The reaction mixture was cooled to room temperature and washed with water. The toluene layer was separated and concentrated under reduced pressure. Analysis of the resulting product revealed that it contains the compound (I) in a purity of about 77% and a large amount of a compound of the following formula as the impurity:

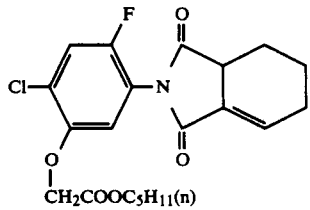

Purification of the above product by silica gel column chromatography gave the compound (I) (13.7 g).
Yield: 77.9%.
Purity: 98.2%.

COMPARATIVE EXAMPLE 7

A mixture of the compound (II) (12.0 g), 3,4,5,6-tetrahydrophthalic anhydride (7.56 g), p-toluenesulfonic acid (0.4 g) and toluene (24 g) was refluxed for 10 hours, during which water was azeotropically removed. The reaction mixture was treated in the same manner as in Example 4 to give the compound (I) (15.6 g).
Yield: 88.9%.
Purity: 80.9%.

Still, the product contained a large amount of a compound of the formula as the impurity:

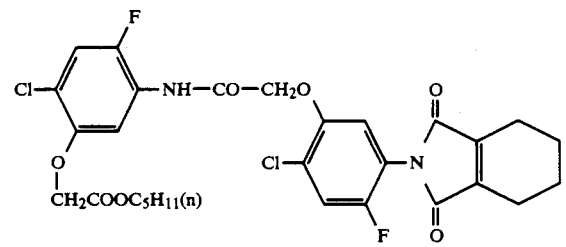

What is claimed is:
1. A 4-Chloro-2fluoro-5-(pentyloxycarbonylmethyloxy)nitrobenzene compound of the formula:

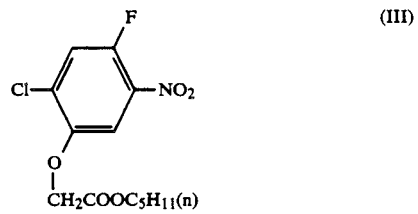

* * * * *